United States Patent [19]

McRae

[11] Patent Number: Plant 5,952

[45] Date of Patent: Apr. 21, 1987

[54] ASIATIC LILY NAMED IMPACT

[75] Inventor: Edward A. McRae, Boring, Oreg.

[73] Assignee: Melridge, Inc., Gresham, Oreg.

[21] Appl. No.: 710,319

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmux

[57] ABSTRACT

A new variety of hybrid Asiatic lily having flowers of large size and excellent form particularly characterized by their unusual combination of rich golden orange color brushmarked with deep magenta-purple presenting an intense and unusual color pattern that is new in the upright Asiatic division of lilies, the flowers being borne on a single stem in a large and compact raceme. This plant is highly resistant to disease, shows high tolerance to virus, and is an excellent garden plant with blooms having long persistence both on the plant and as cut-flowers. Also, the bulbs of this new plant may be precooled for cut-flower production.

1 Drawing Figure

BACKGROUND OF THE NEW PLANT

This new variety of lily plant originated as a seedling selected from a group of seedlings produced at Sandy, Oreg., by using the cultivar "Connecticut King" (unpatented) as the seed parent and an unnamed seedling having the parentage (*Lilium leichtlinii* var. *maximowiczii* f. unicolor×*L. dauricum*)$F_2$ as the pollen parent, this crossing having been done in the course of breeding efforts carried on by me since the year 1974 with the object of producing superior upright-flowering Asiatic lilies in shades of orange and golden orange and having dramatic brushmarks, the plants themselves being suited to cut-flower production.

The flowers of my new lily plant are particularly characterized by their large size with very broad tepals of thick texture having a golden orange color tone with each tepal having a deep magenta-purple brushmark beginning just above the nectaries and extending for about 2 to 3 cm. with a width of about 2 cm. At the base of each brushmark and on each side of the nectaries, a small number of normally pigmented papillae may be found. In addition, this new lily plant possesses to a high degree the desirable characteristics of hybrid vigor, great hardiness, a high degree of disease resistance, and a vigorous growth habit as observed at Sandy, Oreg. This new lily variety has been asexually reproduced by me and under my direction at Sandy, Oreg., and successive generations produced by bulb-scale propagation and natural propagation from bulblets have demonstrated that the novel and distinctive characteristics of this new plant hold true under asexual propagation from generation to generation and appear to be firmly fixed.

DESCRIPTION OF THE DRAWING

My new variety of lily plant is illustrated by the accompanying photographic drawing which shows a face view of an open bloom showing the flower form and tepal arrangement, the flower having been hand-painted to show the novel and distinctive golden orange color tone marked with large and conspicuous magenta-purple brushmarks on each of the tepals which are displayed in a star arrangement.

DESCRIPTION OF THE NEW VARIETY

The following is a detailed description of my new variety of Asiatic hybrid lily, with color designations according to The R.H.S. Colour Chart published by The Royal Horticultural Society of London, England, and with nomenclature according to The International Lily Register, 2nd edition, of The Royal Horticultural Society.

THE PLANT

Origin: Seedling.

Parentage:

- *Seed parent.*—"Connecticut King" (unpatented).
- *Pollen parent.*—An unnamed brushmarked seedling of parentage (*Lilium leichtlinii* var. *maximowiczil* f. unicolor×*L. dauricum*)$F_2$.

Classification:

- *Horticultural.*—Hybrid lily cultivar, Division I-A of the Horticultural Classification of Lilies by The Royal Horticultural Society.
- *Commercial.*—Upright Asiatic hybrid lily.

Form: A single stem, erect, and stately.

Height: About 90 to 115 cm. from bulbs of about 12 to 15 cm. in circumference.

Growth: Vigorous and upright.

Foliage:

- *Quantity.*—Abundant.
- *Leaf size.*—About 8 to 15 cm. long and 1 to 3 cm. wide at the base.
- *Leaf shape.*—Lanceolate with entire margins.
- *Texture.*—Leathery.
- *Aspect.*—Glossy.
- *Color.*—Dark green.

Bulbs:

- *Size.*—Ranging to 25 cm. in circumference for commercial use.
- *Color.*—White.

THE BUD

Form: Long ovoid with obtuse tip.

Size: About 7 to 9 cm. long just prior to opening.

Opening rate: The bud opens slowly at maturity, in response to light.

Color: Golden Orange, RHS 24C, when tepals first divide and when they begin to unfurl.

Peduncle:

*Length.*—About 7 to 19 cm., depending upon light levels.

*Color.*—Deep green.

THE FLOWER

Blooming habit: Annually; once, and profusely, in mid-season for Asiatic lilies. October-dug bulbs properly precooled, when planted in February under glass in western Oregon, with no supplementary lighting, flower in an average of about 80 days when grown at moderate glasshouse temperatures.

Size: Large; about 14 to 18 cm. in diameter.

Borne: About 6 to 9 as a compact raceme on a single stem.

Shape: Flat to slight cup-shaped; tepal tips lightly recurved, and slightly incurved margins.

Tepalage:

*Number.*—Six.

*Arrangement.*—As an open six-pointed star with tepal margins very slightly overlapping.

*Appearance.*—The flower is shiny.

*Color.*—The base color is Golden Orange, RHS 28A, and each tepal is marked with a deep magenta-purple brushmark having the appearance of RHS 187A, beginning above the nectary furrow and extending about 2 to 3 cm. along the midrib and with a width of about 2 cm. or more.

*Spotting.*—In addition to the brushmark, a small number of magenta-purple spots are found on each side of the nectary below the brushmarks.

*Tepal longevity.*—The tepals stay on the stem about three weeks and there is no color change.

Pedicel:

*Length.*—About 4 to 6 cm.

*Form.*—Sturdy and upright.

*Color.*—Deep green.

Fragrance: None.

Disease resistance: The flower and plant are resistant to disease being particularly resistant to Fusarium and Botyrytis.

Lasting Quality: The flower is long lasting, about 2 to 3 weeks both on the plant and as a cut flower.

THE REPRODUCTIVE ORGANS

Stamens:

*Number.*—Six.

*Arrangement.*—Typical of genus Lilium.

Anthers:

*Color.*—Greyed Red, RHS 178A.

Filaments:

*Length.*—About 5 cm.

*Color.*—Soft gold.

Pollen:

*Color.*—Same as anthers.

Pistils:

*Number.*—One.

Style:

*Length.*—About 5 cm.

Stigma:

*Color.*—Dark plum.

Character of ovary: Typical of genus Lilium.

THE FRUIT

Fertility: The fruit is fertile.

Shape: Ovoid.

Color at maturity: Soft brown, sometimes overlaid with plum.

This new variety of Asiatic lily most nearly resembles "Picasso" (U.S. Plant Pat. No. 5 007) but with much larger and more intense brushmarks. Also, it has broader flower tepals.

I claim:

1. A new and distinct variety of Asiatic hybrid lily, substantially as herein shown and described, characterized by the excellence of its flower form and substance and in particular by its unusual and dramatic color pattern of golden orange flowers, each tepal of which is marked with a very large and intensely colored deep magenta-purple brushmark; and by its vigorous growth and propagation characteristics with versatility as both a garden plant and a plant grown from precooled bulbs for cut-flower production.

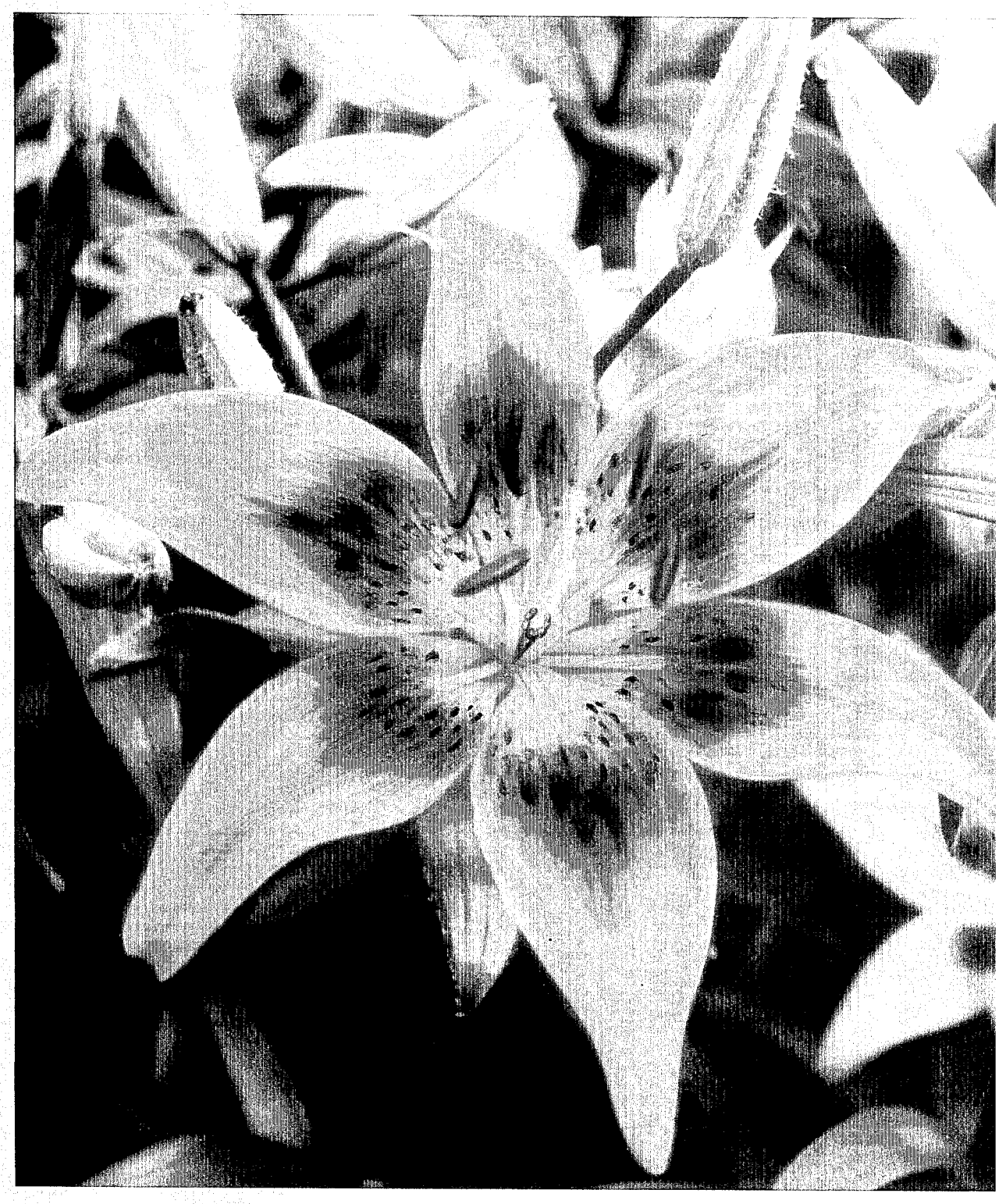

* * * * *